US011217336B2

(12) United States Patent
Anthony et al.

(10) Patent No.: US 11,217,336 B2
(45) Date of Patent: Jan. 4, 2022

(54) AUTOMATED MEDICATION DISPENSING UNIT

(71) Applicant: Alixa Rx LLC, Plano, TX (US)

(72) Inventors: Philip M. Anthony, Chicago, IL (US);
Huan Nguyen, Lantana, TX (US);
Ronald Silva, San Francisco, CA (US);
Larry Deans, Plano, TX (US);
Maryann Tomechko, Plano, TX (US)

(73) Assignee: Alixa Rx, LLC, Plano, TX (US)

( * ) Notice: Subject to any disclaimer, the term of this patent is extended or adjusted under 35 U.S.C. 154(b) by 808 days.

(21) Appl. No.: 14/046,353

(22) Filed: Oct. 4, 2013

(65) Prior Publication Data
US 2014/0097195 A1 Apr. 10, 2014

Related U.S. Application Data

(63) Continuation-in-part of application No. 13/646,598, filed on Oct. 5, 2012.

(60) Provisional application No. 61/711,201, filed on Oct. 8, 2012.

(51) Int. Cl.
*G06F 19/00* (2018.01)
*G16H 20/13* (2018.01)

(52) U.S. Cl.
CPC .................. *G16H 20/13* (2018.01)

(58) Field of Classification Search
CPC ........... B65B 5/103; B65B 7/14; B65B 35/06; G06F 19/3462; G07F 11/005; G07F 17/0092; G16H 20/13
See application file for complete search history.

(56) References Cited

U.S. PATENT DOCUMENTS

| | | | | |
|---|---|---|---|---|
| 2,701,991 A | * | 2/1955 | Croucher | B41B 17/06 276/13 |
| 4,967,928 A | * | 11/1990 | Carter | G16H 20/13 221/2 |
| 5,412,372 A | | 5/1995 | Parkhurst et al. | |

(Continued)

OTHER PUBLICATIONS

PCT International Search Report dated Mar. 6, 2014 of International Application No. PCT/US2013/063471. 14 Pages.

*Primary Examiner* — Gene O Crawford
*Assistant Examiner* — Kelvin L Randall, Jr.
(74) *Attorney, Agent, or Firm* — Barcelo, Harrison & Walker LLP

(57) ABSTRACT

In certain embodiments, a remote automated dispensing unit (ADU) may include an enclosed cabinet, one or more locking mechanisms to keep the cabinet secure, one or more doors on the cabinet to allow access to the internal components, and a computer system that manages the dispensing of inventory. The ADU may include a mechanism for the dispensing of medications for individual patients including: one or more canisters for storing medications, one or more canister base stations for securing the one or more canisters to the ADU, and a chute and funnel system for the guidance of medications as they fall from the canisters into a packaging station for packaging medications into packages for particular patients. One or more sensors may be used to detect misdispensing of medications, and a combination of sensors and operating sequences may be used to reduce the amount of misdispensed medication.

17 Claims, 7 Drawing Sheets

(56) References Cited

U.S. PATENT DOCUMENTS

| | | | |
|---|---|---|---|
| 5,671,787 A * | 9/1997 | Wehrmann | B65B 57/20 141/131 |
| 5,801,632 A * | 9/1998 | Opal | H04M 11/04 340/585 |
| 6,256,963 B1 * | 7/2001 | Kim | B65B 5/103 221/265 |
| 6,332,100 B1 | 12/2001 | Sahai et al. | |
| 6,799,684 B2 * | 10/2004 | Wooldridge | B07C 5/38 209/551 |
| 8,386,073 B2 * | 2/2013 | Kim | B65B 5/103 221/167 |
| 8,393,495 B2 * | 3/2013 | Kim | B65B 5/103 221/10 |
| 8,700,208 B2 * | 4/2014 | Kim | B65B 35/14 198/757 |
| 8,985,389 B2 * | 3/2015 | Yuyama | A61J 7/02 221/224 |
| 2003/0034373 A1 * | 2/2003 | Yuyama | B26D 3/30 225/96.5 |
| 2003/0057225 A1 * | 3/2003 | Kim | B65B 5/103 221/92 |
| 2003/0105554 A1 | 6/2003 | Eggenberger et al. | |
| 2005/0111724 A1 * | 5/2005 | Macy | G06M 1/101 382/141 |
| 2006/0025884 A1 * | 2/2006 | Henkel | B65B 5/103 700/216 |
| 2006/0058724 A1 * | 3/2006 | Handfield | A61J 7/0084 604/20 |
| 2006/0124656 A1 * | 6/2006 | Popovich, Jr. | G07F 9/026 221/9 |
| 2006/0259188 A1 * | 11/2006 | Berg | A61J 7/0084 700/231 |
| 2006/0265102 A1 * | 11/2006 | Bain | G07F 11/62 700/237 |
| 2006/0273106 A1 * | 12/2006 | Kim | B65B 5/103 221/200 |
| 2008/0136649 A1 * | 6/2008 | Van De Hey | E03C 1/057 340/573.1 |
| 2008/0148685 A1 * | 6/2008 | Kim | G06Q 20/206 53/77 |
| 2009/0218363 A1 | 9/2009 | Terzini | |
| 2010/0096399 A1 * | 4/2010 | Ratnakar | G07F 11/44 221/1 |
| 2010/0200448 A1 * | 8/2010 | Doi | G07D 9/00 206/459.1 |
| 2011/0303692 A1 * | 12/2011 | Kim | B65B 5/103 221/1 |
| 2011/0313566 A1 * | 12/2011 | Kim | B65B 5/103 700/231 |
| 2012/0006843 A1 | 1/2012 | Kim | |
| 2012/0095593 A1 * | 4/2012 | Clarke | G07F 11/005 700/231 |
| 2012/0159907 A1 * | 6/2012 | Henkel | B65B 5/103 53/500 |
| 2012/0239186 A1 * | 9/2012 | Kim | G07F 11/26 700/232 |
| 2013/0078161 A1 * | 3/2013 | Smith | A61L 2/04 422/292 |
| 2013/0270291 A1 * | 10/2013 | Omura | B65D 83/04 221/92 |
| 2013/0334242 A1 * | 12/2013 | Yuyama | A61J 7/02 221/7 |
| 2014/0150376 A1 * | 6/2014 | Milton | B65B 5/103 53/235 |
| 2015/0127145 A1 * | 5/2015 | Kim | G07F 17/0092 700/235 |

\* cited by examiner

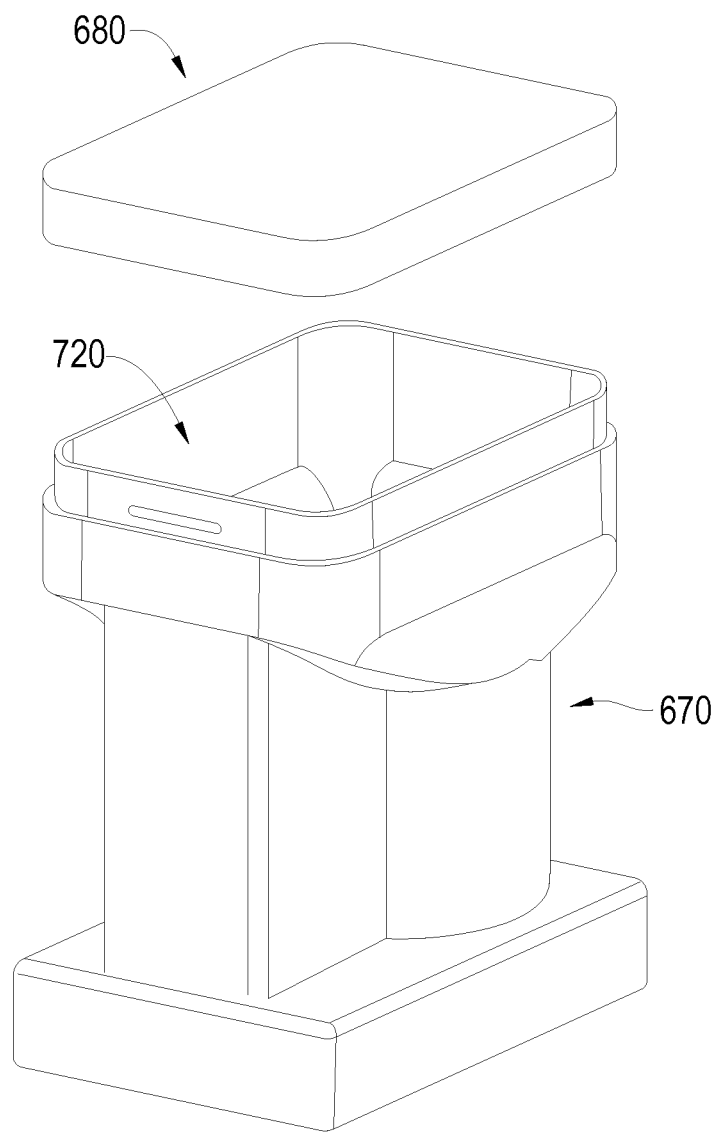
FIG. 7
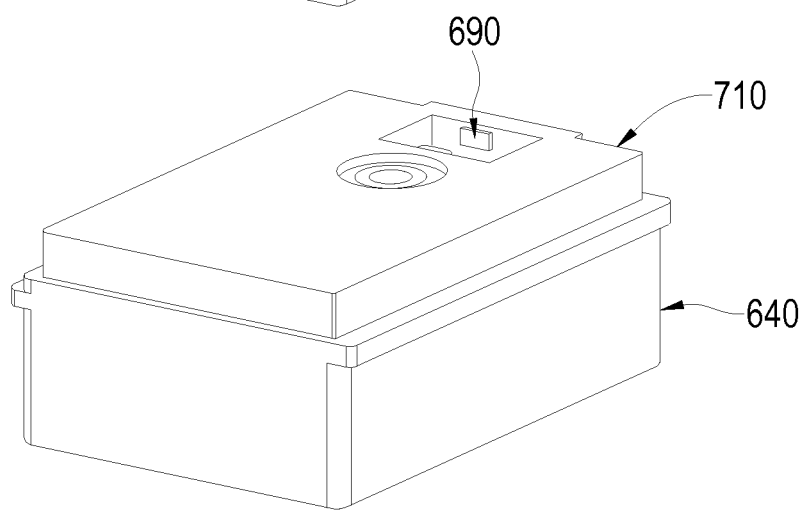

AUTOMATED MEDICATION DISPENSING UNIT

I. CROSS-REFERENCE TO RELATED APPLICATIONS

This application is a continuation-in-part of U.S. patent application Ser. No. 13/646,598, entitled "Locking Canister for Dispensing Medications," filed Oct. 5, 2012, and claims priority to U.S. Patent Application No. 61/711,201, filed Oct. 8, 2012, and entitled "Automated Medication Dispensing Unit." The entirety of each of the foregoing patents, published patent applications and patent applications is incorporated by reference herein.

II. FIELD OF THE INVENTION

The disclosure generally relates to systems and methods for dispensing medication and more particularly to an automated dispensing unit for retaining and selectively dispensing medications.

III. BACKGROUND OF THE INVENTION

A wide variety of medications are currently on the market. Many medications are carefully regulated and may be approved for use for particular conditions and may require a prescription prior to dispensing. Some drugs may have significant monetary value, creating a risk of diversion for profit or misappropriation for unapproved uses. Some drugs, such as pain killers including but not limited to narcotics, may be prone to abuse increasing the risk of theft or diversion if not properly monitored and secured throughout the medication administration process from production to initial receipt to dispensing and administration to patients.

There is a need to address the foregoing deficiencies in the art.

IV. BRIEF DESCRIPTION OF THE DRAWINGS

FIG. 7 depicts a perspective exploded view of a canister housing hovering above a canister base station and a canister top hovering on top of the canister housing.

V. DETAILED DESCRIPTION

Figure 1:
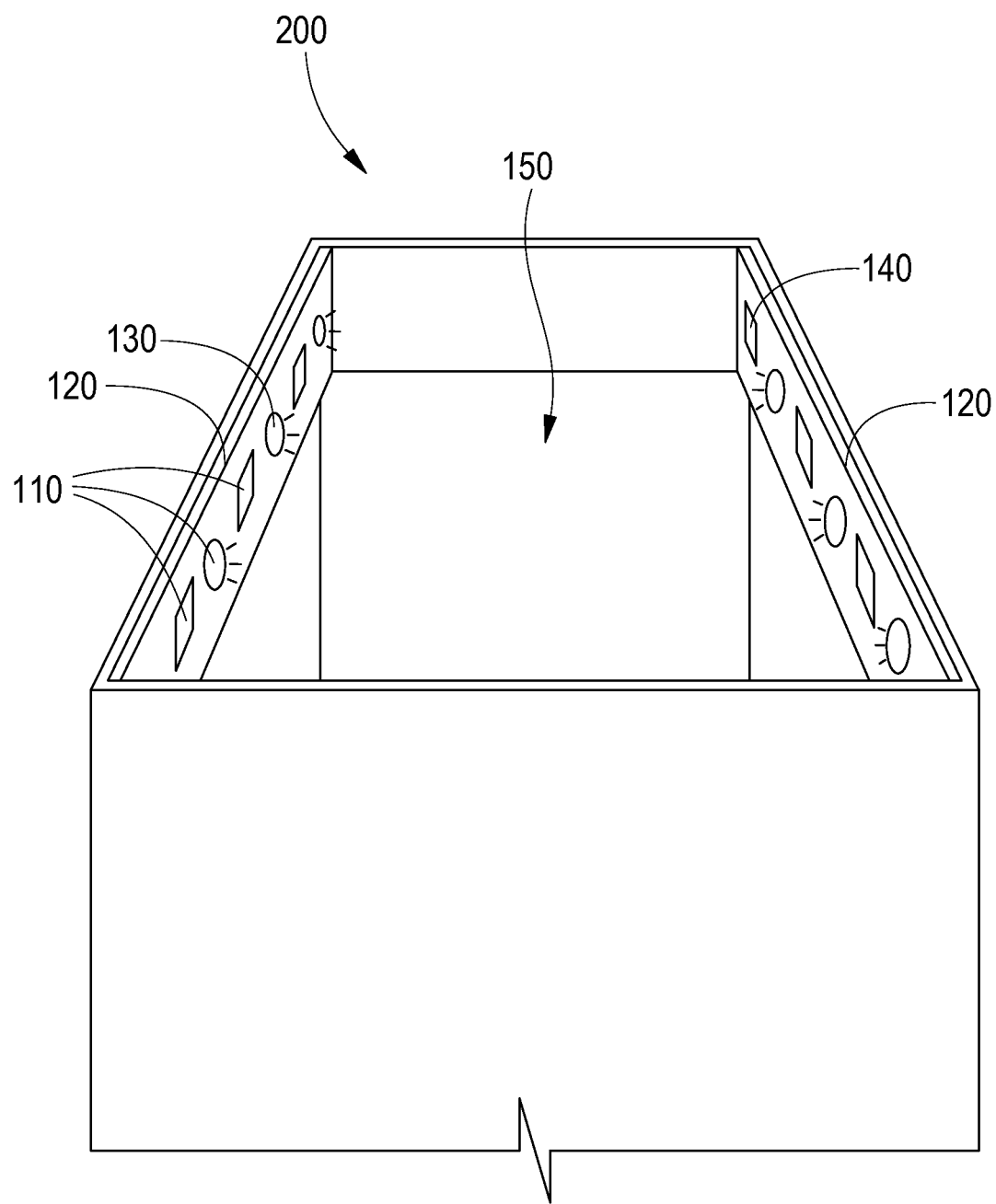
FIG. 1 depicts a perspective view of a hopper assembly in accordance with certain embodiments.

In certain embodiments, a machine for dispensing pharmaceuticals is disclosed, comprising: one or more canisters for containing one or more doses of medication; one or more medication release mechanisms for selectively releasing a selected one or more doses of medication from the one or more canisters; and a hopper comprising: a volume for receiving one or more doses of medication released from the one or more canisters; one or more sensors for detecting the release of the one or more doses of medication into the volume; and a first mechanism for releasing the one or more doses of medication to a packaging mechanism if the detected one or more doses matches the selected one or more doses. The one or more sensors may comprise multiple sensors for detecting the release of the one or more doses of medication into the volume. The multiple sensors may be read in series. The multiple sensors may be read in parallel. The hopper may further comprise: a second mechanism for releasing the one or more doses of medication to a holding receptacle if the detected one or more doses do not match the selected one or more doses. The holding receptacle may comprise a locking mechanism. The machine may further comprise one or more sensors for detecting the position of the first mechanism. The machine may further comprise one or more sensors for detecting the position of the second mechanism. The first mechanism may be configured for releasing the one or more doses of medication to a packaging mechanism if the detected one or more doses matches the selected one or more doses and for releasing the one or more doses of medication to a holding receptacle if the detected one or more doses do not match the selected one or more doses. The one or more sensors may detect the quantity and type of the one or more doses of medication. The one or more sensors may detect the type of the one or more doses of medication by comparing a digital image of the one or more doses of medication captured by the one or more sensors with one or more images of known medications. The one or more sensors may comprise one or more sensors at a top opening of the hopper to detect when more than one medication falls into the hopper. The canister may comprise a canister locking mechanism for preventing the unauthorized release of medication from the canister. The canister locking mechanism may be configured to lock the canister before removal from the machine. The medication release mechanism may comprise a retractable portion, the retractable portion having a closed position and a retracted position and may be configured to be selectively moved from the closed position to the retracted position to dispense one or more doses of medication from the canister. The retractable portion may comprise a shutter. The medication release mechanism may comprise one or more locking mechanisms configured for locking the retractable portion in at least one of the closed and the retracted position. The one or more locking mechanisms may be configured to lock the retractable portion in the closed position before the canister can be removed from the machine. The at least one of the one or more locking mechanisms may comprise a worm gear for selectively rotating the retractable portion between the closed position and the retracted position. The at least one of the one or more locking mechanisms may comprise a worm gear for selectively locking the retractable portion in at least one of the closed position and the retracted position. The hopper may comprise one or more separating elements to randomly divert each released dose of medication into one of a plurality of channels.

In certain embodiments, a method of dispensing medication from a machine is disclosed, comprising: providing one or more canisters comprising one or more medication release mechanisms for selectively releasing one or more doses of medication from the one or more canisters and containing one or more doses of medication; connecting the one or more canisters to one or more base stations; releasing a selected one or more doses of medication from the one or more canisters into a hopper; detecting the release of one or more doses of medication into the hopper; and releasing the one or more doses of medication to a packaging mechanism if the detected one or more doses matches the selected one or more doses of medication. The one or more canisters may comprise one or more canister locking mechanisms for preventing the unauthorized release of doses of medication from the one or more canisters. The method may further comprise locking the one or more canisters. The method may further comprise keeping the one or more canisters locked until the release of a first dose of medication is authorized. The method may further comprise keeping the one or more canisters locked until one or more doors enclosing the one or more containers are locked. The one or more doors may not be able to be unlocked until the one or more canisters are locked. The step of detecting may comprise continuously monitoring for a period of time to detect the release of one or more doses of medication. The method may further comprise locking at least one canister and removing the at least one canister from the machine. The method may further comprise releasing the one or more doses of medication to a holding receptacle if the detected one or more doses do not match the selected one or more doses. The at least one of the medication release mechanisms may comprise a retractable portion, the retractable portion having a closed position and a refracted position. The step of releasing may comprise moving the retractable portion from the closed position to the retracted position to dispense one or more doses of medication from the canister. The retractable portion may comprise a shutter. The method may further comprise locking the retractable portion in at least one of the closed and the retracted position. The locking mechanism may comprise a worm gear for selectively moving the retractable portion between the closed position and the refracted position. The locking mechanism may comprise a worm gear for selectively locking the retractable portion in at least one of the closed position and the retracted position. The step of sensing may be performed continuously for a period of time. The step of releasing may comprise: releasing a first dose of medication; and releasing a second dose of medication after the first dose of medication has been detected by one or more sensors. The step of releasing may comprise: releasing a first dose of medication; and releasing a second dose of medication after the first dose of medication has been detected by one or more sensors and released to the packaging mechanism. The method may further comprise remote monitoring for unauthorized access to the one or more canisters. The method may further comprise receiving authorization before opening one or more doors of the machine for accessing the one or more canisters.

In certain embodiments, a machine for dispensing pharmaceuticals is disclosed, comprising: one or more canisters for containing one or more doses of medication; one or more medication release mechanisms for selectively releasing a selected one or more doses of medication from the one or more canisters; one or more sensors each located proximate an exit opening of one of the one or more canisters for detecting the release of one or more doses of medication from the one or more canisters, and a hopper comprising: a volume for receiving one or more doses of medication released from the one or more canisters; one or more sensors for detecting the release of the one or more doses of medication into the volume; and a first mechanism for releasing the one or more doses of medication to a packaging mechanism if the detected one or more doses matches the selected one or more doses. The one or more sensors may comprise multiple sensors for detecting the release of the one or more doses of medication into the volume. The multiple sensors may be read in series. The multiple sensors may be read in parallel.

Figure 4:
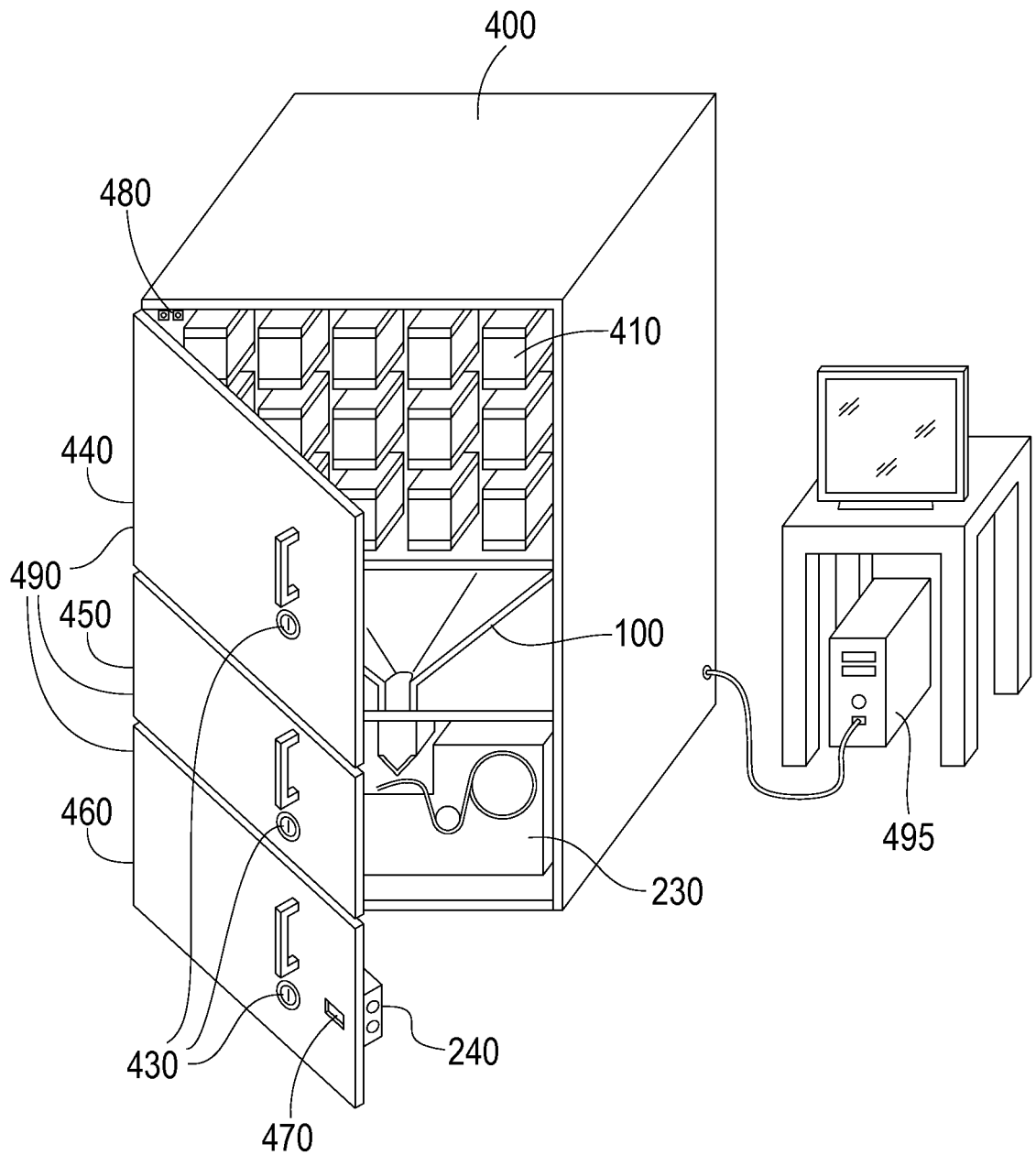
FIG. 4 depicts a perspective view of an automated medication dispensing unit in accordance with certain embodiments.
Figure 5:
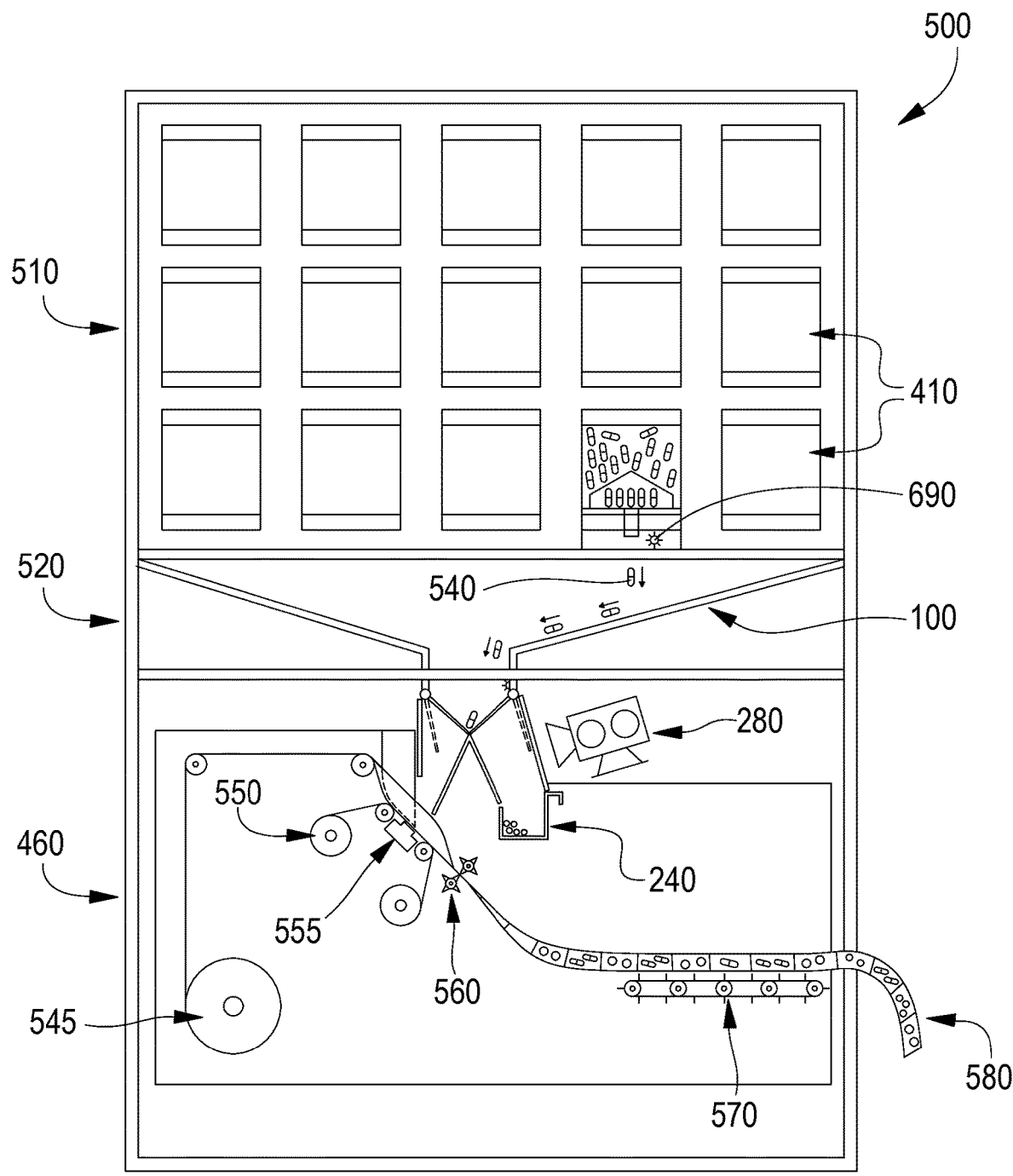
FIG. 5 depicts a side view of an automated medication dispensing unit in accordance with certain embodiments.

In certain embodiments as shown in FIGS. 4 and 5, a remote automated dispensing unit (ADU) 400 may include an enclosed cabinet 500, one or more locking mechanisms 430 to keep the cabinet 500 secure, one or more doors 490 on the cabinet 500 to allow access to the internal components, a computer system 495 that manages the dispensing of inventory (which may include without limitation patient prescription information, security measures for the ADU machine 400, data and communications link to the pharmacy, and control of the machine operation including dispensing process). The ADU 400 may include a mechanism for dispensing of medications 540 for individual patients including: one or more canisters 410 for storing medications 540, one or more canister base stations 640 for securing the one or more canisters 410 to the ADU 400, a chute and funnel system 200 for the guidance of medications 540 as they fall from the canisters 410 into a hopper 200 that detects the medications 540 before dropping the medications 540 into a packaging station 230 for packaging medications 540 into packages 580 for particular patients.

Figure 6:
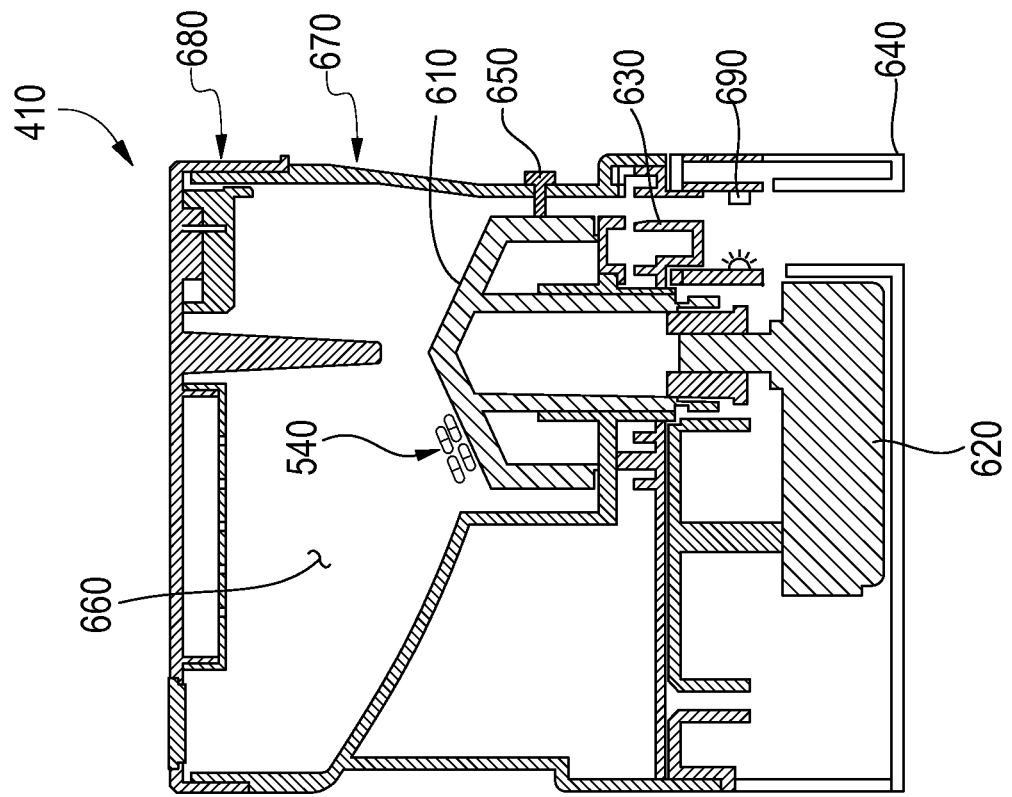
FIG. 6 depicts an end view and cutaway side view of a canister in accordance with certain embodiments.
Figure 6:
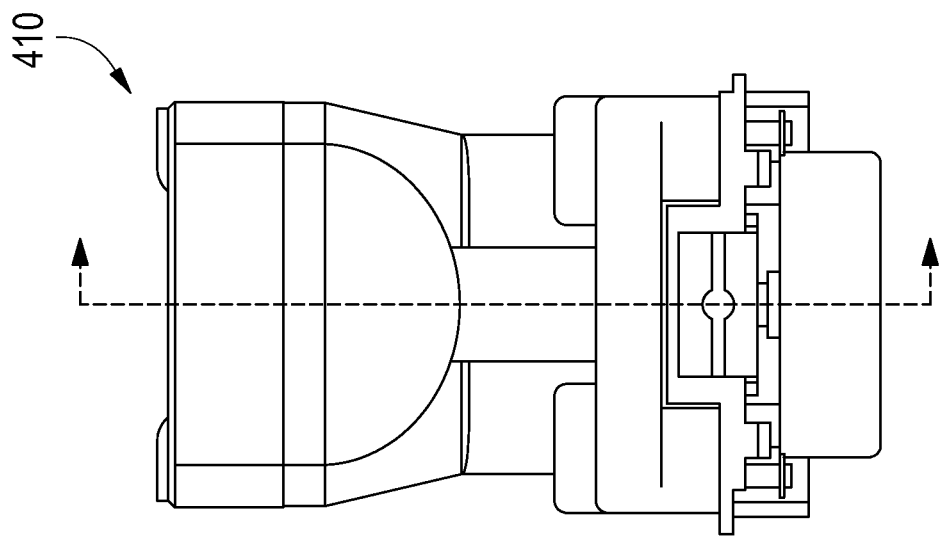

In certain embodiments as shown for example in FIGS. 6 and 7, the one or more canister assemblies may include: one or more canisters 410 each including a housing with an inner volume 660 and an outer surface 670, an opening 720 on the top surface, an opening in the bottom for the dispensing of individual medications 540, and a small opening on one side; a top cover 680 that slides or snaps onto the top of the housing 670 to keep the medications 540 secure within the canister housing volume 660; a stopper 650 that may be inserted into a small opening on the side of the housing 670 to allow only one medication 540 to be dispensed at a given time, and an indexing wheel 610 that sits inside the housing 670. The indexing wheel 610 may have a multitude of vertical slots on the sides, the indexing wheel 610 having a cylindrical boss protruding from the bottom of the component that sticks through a circular opening in the bottom of the volume 660 in the housing 670 to guide the indexing wheel 610 while it spins during operation; a means for securing the indexing wheel 610 to the canister housing 670, a chute or guide 630 attached to the housing 670 at the opening where medications 540 fall through when dispensed. The guide may be sized to allow only one medication 540 to pass through the opening at a time in a direction that ensures that the medications pass by a sensor 690 to sense when each individual medication 540 is dispensed. The canister base station 640 may include a housing 670, a motor 620, electrical connections (wires) to a control system 495 that tells the motor 620 when to spin and dispense a medication 540 through pill guide 630, and one or more sensors 690 to detect when each individual medication 540 is dispensed from the canister 410. The chute and funnel system may have a funnel 100 configured for the guidance of medications 540 as they fall from the canisters 410 such that the funnel 100 guides the medications 540 into the hopper 200 above the packaging station 230. The packaging station 230 may package one or more medications 540 into individual packets 580, which may include without limitation plastic heat sealed film. The plastic packets 580 may have a surface that can have information printed on it or a label applied to it with patient and prescription medication information.

In certain embodiments, an ADU 400 may include a mechanism for dispensing medications for individual patients including: a canister assembly that stores medications. The canister assembly 410 may include a housing with an inner volume 660 and an outer surface 670, an opening 720 on the top surface, an opening in the bottom for the dispensing of individual medications 540, and a small opening on one side, a top cover 680 that slides or snaps onto the top of the housing 670 to keep the medications 540 secure within the canister housing volume 660; a stopper 650 that is inserted into the small opening on the side of the housing 670 that allows only one medication 540 to be dispensed at a given time through pill guide 630; an indexing wheel 610 that sits inside the housing 670, the indexing wheel 610 having a multitude of vertical slots on the sides, the indexing wheel 610 having a cylindrical boss protruding from the bottom of the component that sticks through a circular opening in the bottom of the volume 660 in the housing 670 for the guidance of the indexing wheel 610 while it spins during operation; means for securing the indexing wheel 610 to the canister housing 670 such as a retaining ring or one or more snap-ribs on the indexing wheel boss; a chute or guide 630 attached to the housing 670 at the opening where medications 540 fall through when dispensed, the guide sized to allow only one medication 540 to pass through the opening at a time in a direction that ensures that the medications 540 pass by a sensor 690 to sense when each individual medication 540 is dispensed. The ADU 400 may comprise one or more canister base stations 640 for coupling to the one or more canisters 410. The one or more base stations 640 may include a housing 670, a motor 620, electrical connections (wires) to the control system 495 that tells the motor 620 when to spin and dispense a medication 540, and one or more sensors 690 to detect when each individual medication 540 is dispensed from the canister 410. In certain embodiments, a chute and funnel system may have a funnel 100 that may be used for the guidance of medications 540 as they fall from the canisters 410, the chute and funnel 100 may guide the medications 540 into a packaging station 230 for packaging the medications 540 into individual packets 580 (plastic heat sealed pouches). The individual packets 580 may include plastic packets with a surface that can have information printed on it or a label applied to it with patient and prescription medication information.

In certain embodiments, an ADU 400 may include a hopper assembly 200 that may include: one or more sensors 110 to detect when each individual medication 540 drops into the hopper 200, a volume 150 in the hopper 200 that receives the medications 540, one trap door 220 that diverts the medications into the packaging station 230 if the sensor(s) 110 on the top of the hopper 200 confirm that the correct medications 540 have fallen into the hopper 200; a second trap door 210 that diverts the medications 540 into a secure locked drawer 240 if an incorrect medication 540 or incorrect number of medications 540 drop into the hopper 200, two motors that each open one of the two trap doors to separate exit chutes (one to the packaging station 230/the other to the secure locked drawer 240).

The canister 410 may have a vibrator that helps to ensure that medications 540 do not get caught on the ledges within the housing 670. The canister 410 may have an RFID tag with both reprogrammable memory and permanent memory to allow for the identification of individual canisters 410 and to store information related to canister contents.

Each of the foregoing features may be combined with each other and with each of the embodiments that follow. By combining multiple features in various embodiments, the security and accuracy of the ADU may be improved as compared to ADUs incorporating single security or accuracy improving features. In certain embodiments, multiple features may be implemented together to maximize the security and accuracy of the machine by reducing the number of misdispensed medications getting through to the patient packets 580.

In certain embodiments, one or more locking canisters may be utilized with a locking top cover and an electronic lock system for an exit opening at the bottom of the canister from which medications may be dispensed. Various embodiments of locking containers that may be used in certain embodiments are disclosed in greater detail in related U.S. patent Ser. No. 13/646,598, entitled "Locking Canister For Dispensing Medications," and filed on 5 Oct. 2012, which is incorporated by reference herein in its entirety.

For example and without limitation, a locking canister may include an electronic lock system for the bottom opening including: an electric motor (including but not limited to options such as a stepper motor, brush DC motor, AC motor, or brushless DC motor), a worm gear on the motor shaft, a shutter with the following elements: a worm gear with a rack profile on one edge, a hole in the center to guide the shutter so that it spins around a boss on the bottom of the canister housing, a wall or face that covers the opening in the bottom of the canister when the shutter is in the closed position, and an opening that lines up with the opening in the bottom of the canister when the shutter is in the open position, allowing medications to fall through the opening when they are dispensed; and a control system (microprocessor) for controlling the motion of the shutter including the stop and start positions.

In certain embodiments as shown in FIG. 1, an ADU 400 may include a hopper 200 with multiple sensors 110 on the top of the hopper 200 (such as but not limited to light sensors), which may be read individually in series or in parallel to detect when multiple medications 540 fall into the hopper 200 at exactly the same time, which if undetected can lead to dispensing the incorrect quantity or type of medications 540 into the patient packets. Multiple sensors 690 (such as but not limited to light sensors) in the canister base station 640 may sense individually in series or in parallel (at the same time) to detect when incorrect medications 540 are dispensed from a canister 410.

Figure 2:
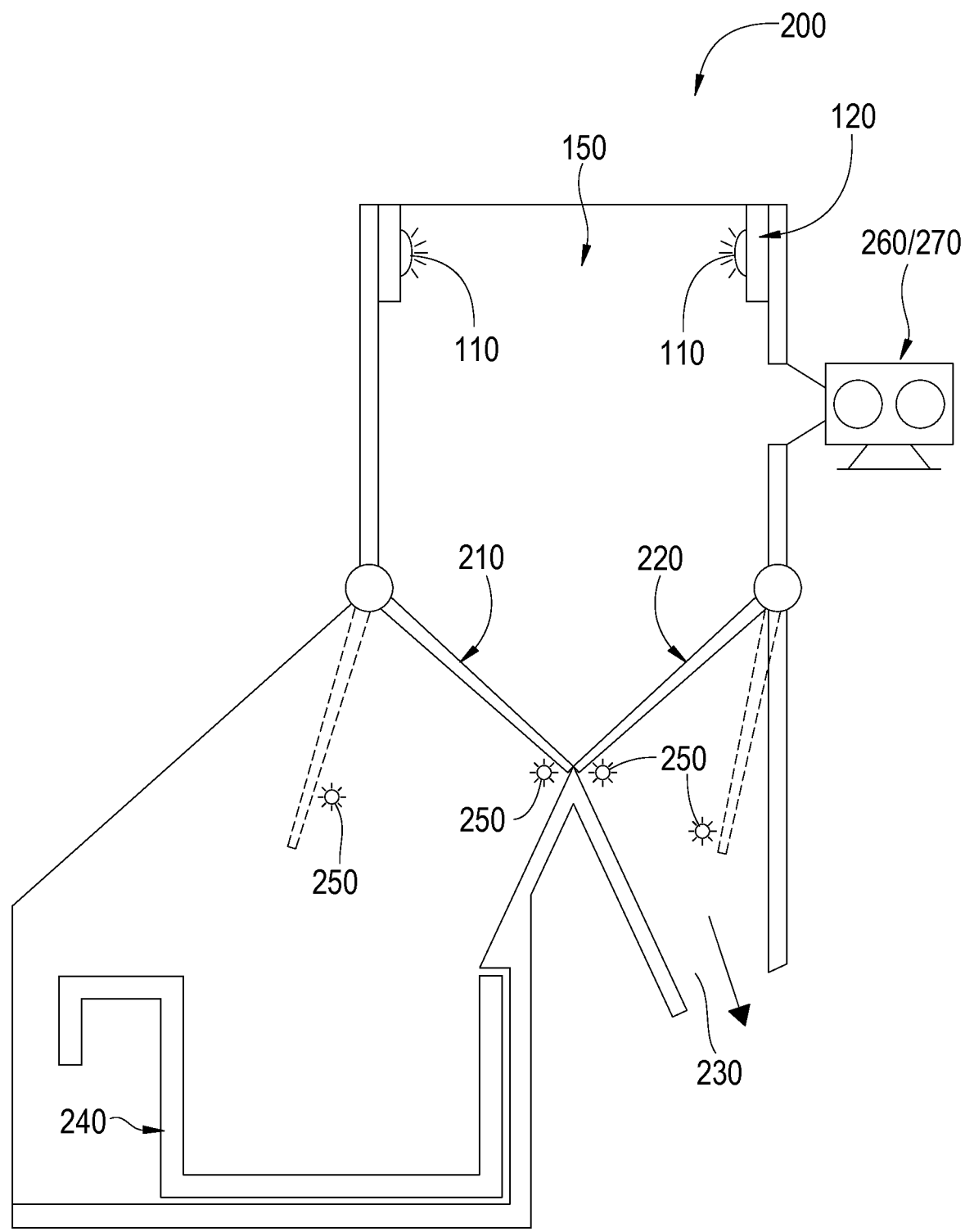
FIG. 2 depicts a cutaway side view of a hopper assembly in accordance with certain embodiments.

In certain embodiments as shown in FIGS. 1 and 2, all sensors 690 in the canister base stations 640 may sense individually at all times to detect when a medication 540 falls inadvertently from a canister 410 at the incorrect time, allowing the hopper 200 to catch such medications 540 and divert them into a secure compartment 240 such that the incorrectly dispensed medications 540 are not dispensed to patient packets 580.

Figure 3:
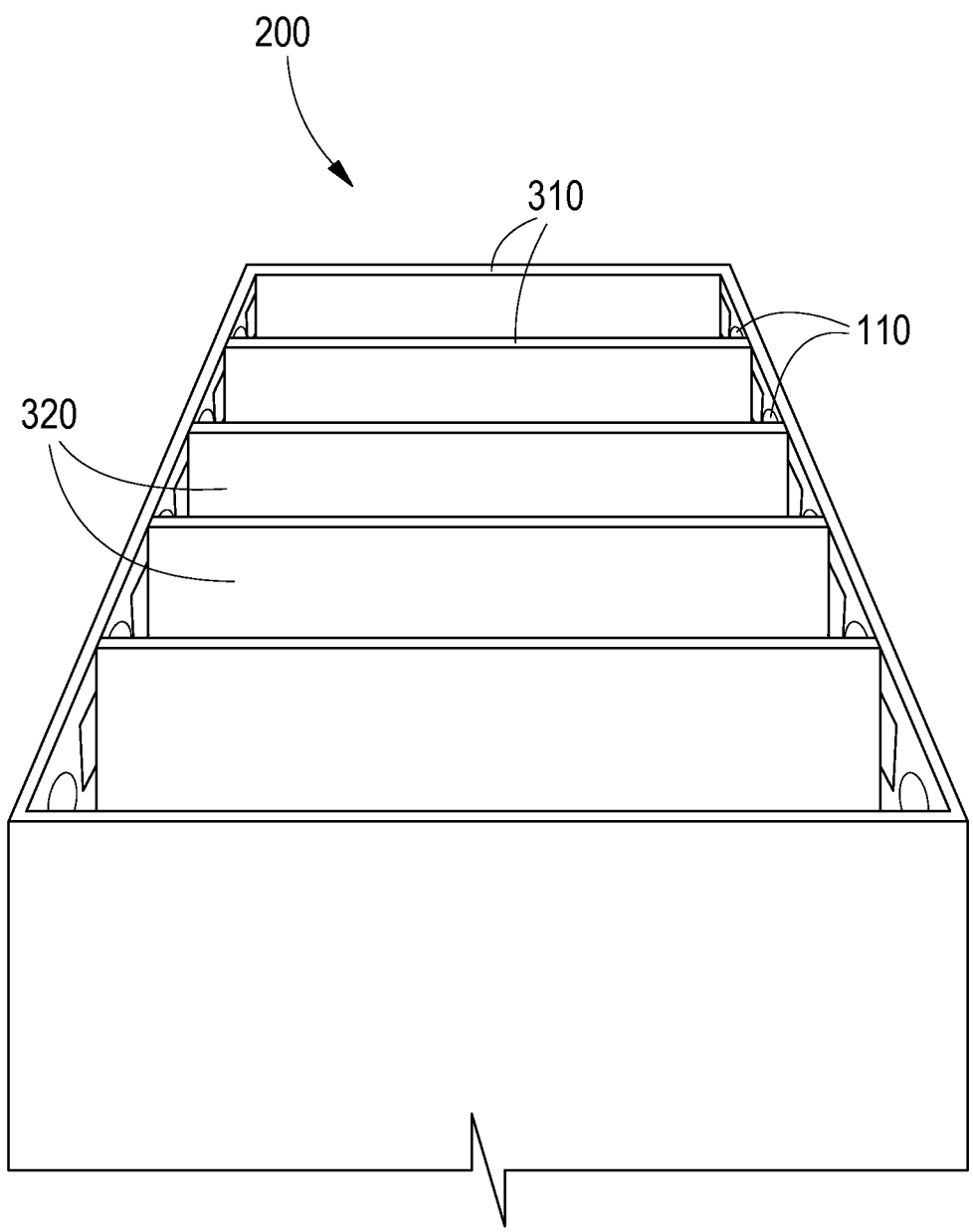
FIG. 3 depicts a perspective view of the top of a hopper assembly in accordance with certain embodiments.

In certain embodiments as shown in FIG. 3, the hopper 200 may have a series of walls 310 built into an opening in the top of the hopper 200 to guide medications 540 as they fall into the hopper 200 through one of the multiple openings 320 created by the walls 310, effectively reducing the frequency of incorrectly dispensed medications 540 that are not detected by the multiple light sensors 110 at the top of the hopper 200 when they fall into the hopper 200 at exactly the same time and immediately next to each other.

In certain embodiments, an ADU 400 may include an operating sequence in the machine that opens a trap door 210 in the hopper 200 that connects to the secure drawer 240 before dispensing any medications such that any medications 540 that inadvertently fell into the hopper 200 when the machine was not operating would be disposed of instead of being dispensed to a patient packet 580.

In certain embodiments, an ADU 400 may include an operating sequence that does not open the electronic lock in the bottom of the canister until it is time to dispense the first medication 540 from the canister 410, as sometimes during transport from the pharmacy to the ADU 400, canisters 410 can vibrate and medications 540 can drop through the opening in the bottom of the canister 410. In certain embodiments, the canister 410 may include a shutter in an electronic locking system that prevents such medications 540 from falling from the canister 410 until the control system 495 in the ADU 400 instructs the machine to dispense the first medication 540 from a canister 410.

In certain embodiments, an ADU 400 may be used for dispensing of medications 540 for individual patients in facilities such as long term care facilities, assisted living facilities, nursing homes, hospitals, shared care facilities, doctors' offices and pharmacies.

In certain embodiments as shown in FIG. 1, an ADU cabinet 400 may include a hopper 200 with one or more sensors 110 positioned at the top opening, a volume 150 in the hopper 200 to catch the medications 540 after they drop into the hopper 200, and one or more mechanisms (such as but not limited to one or more trap doors) to divert medications 540 into the packaging station 230 if the correct medications 540 fall into the hopper 200 and to divert improperly dispensed medications 540 into a secure compartment 240. In certain embodiments, the one or more sensors 110 may be arranged in a left and right sensor bank 120 with one or more emitters 130 and one or more receivers 140. The receivers 140 may be configured to detect the emissions of the emitter 130, which may be altered when one or more doses of medication 540 fall between an emitter 130 and a receiver 140. The combination of one or more emitters 130 and one or more receivers 140 may be used to detect the release of one or more doses of medication 540 from one or more canisters 410 into the hopper 200. A plurality of emitters 130 and a plurality of receivers 140 may be used to improve the accuracy of the machine by reducing the frequency of misdispensed medications 540 that end up in patient packets 580.

In certain embodiments as shown in FIG. 2, the hopper 200 may include one or more sensors 110 positioned at the top opening, a volume 150 in the hopper 200 to catch the medications 540 after they drop into the hopper 200, a first trap door 220 to divert medications 540 into the packaging station 230 if the correct medications 540 fall into the hopper 200, and a second trap door 210 to divert improperly dispensed medications into a secure locked drawer 240. One of ordinary skill in the art will recognize that a variety of mechanisms may be used to perform the diversion of medication 540 to either the packaging station 230 or the secure locked drawer 240, including but not limited to a single trap door. As shown in FIG. 2, the hopper 200 may include one or more sensors 250 for detecting the position of the mechanisms used to divert medications to either the packaging station 230 or the secure compartment 240.

In certain embodiments, a signal from the computer control system 495 may be used to open the trap door 210 that diverts any medications 540 in the hopper volume 150 into the secure locked drawer 240 at the commencement of a batch run to prevent inadvertently dispensed medications 540 that fell from the canisters 410 when the machine 400 was not operating from being dispensed into the first patient packet 580 that is processed during the batch run.

In certain embodiments, the hopper assembly 200 may include a plurality of sensors 110, which may include without limitation light sensors 110 positioned at the top opening of the hopper 200, with each sensor 110 sensing or pulsing continuously for a period of time to detect when more than one medication 540 falls into the hopper 200 at the same time to detect the release of incorrect medications 540 from the one or more canisters 410 to the hopper 200.

In certain embodiments as shown in FIG. 2, the hopper 200 may include a video camera 260 to detect and capture images of medications 540 that fall into the hopper 200. In certain embodiments, the captured images may be compared to a database of images, sizes, and/or colors of existing medications 540 to determine if medication 540 was the correct or incorrect medication 540. In certain embodiments, the hopper 200 may include a digital camera 270 that captures one or more digital images of medications 540 once they land in the hopper 200 combined with a computer system 495 that compares images to a database of images and/or data with sizes, shapes, and/or colors of existing medications 540 to determine if medication 540 was correct or incorrect.

In certain embodiments as shown in FIG. 3, a hopper assembly 200 may include multiple walls or fins 310 in the top opening to randomly divert medications 540 into one of the multitude of channels 320 to reduce the chance of multiple (two or more) medications 540 falling past one sensor 110 at the same time immediately next to each other, to improve the chances of detecting misdispensed medication occurrences.

In certain embodiments, each of the one or more canisters 410 may have a corresponding base station 640 that may include one or more drop sensors 690 to detect one or more doses of medication 540 released from the one or more canisters 410. The one or more drop sensors 690 may be located below a medication release mechanism of one or more of the one or more canisters 410. The one or more drop sensors 690 may be actively sensing for a period of time. The drop sensors 690 may operate independently of each other to detect medications 540 that are inadvertently and/or incorrectly dispensed from a canister 410 to prevent incorrectly dispensed medications 540 from being dispensed into patient packets 580. In certain embodiments, a computer control system 495 which may include a processor may work with the drop sensors 690 to detect the release of incorrect medications 540 and generate a signal to divert any incorrectly dispensed medications 540 into the secure locked drawer 240 instead of into the patient packet 580.

In certain embodiments, only one medication 540 may be dispensed at a time, and the next medication 540 may not be dispensed until the prior medication 540 is sensed by the drop sensors 690 in the base station 640 and the one or more sensors 110 at the top of the hopper 200. This sequence may further improve the accuracy of the overall system by reducing the chances of incorrectly dispensed medications 540 from passing through the sensor banks 120 undetected. In certain embodiments, the next medication 540 may not be dispensed until the prior medication 540 is sensed by the drop sensors 690 in the base station 640 and the sensor bank 120 at the top of the hopper 200. In certain embodiments, each individual medication 540 may be dispensed from the hopper 200 into the patient packet 580 before the next medication 540 is dispensed from its canister 410. This sequence may reduce the number of medications 540 that are dispensed into the secure locked drawer 240 and eventually dispensed into controlled waste. If one medication 540 is not dispensed at a time, multiple medications 540 collect in the hopper 200 until the packet 580 is ready for packaging. If multiple medications 540 are waiting in the hopper 200 for another pill 540, but an incorrect medication 540 falls into the hopper 200, then all of the contents in the hopper 200 may be dispensed into the secure locked drawer 240. By transferring one dose of medication 540 to the packaging mechanism 230 at a time, the cost of the medications 540 that are dispensed into the secure compartment 240 may be reduced.

In certain embodiments, one or more medication release mechanisms on the one or more canisters 410 may remain closed and may also remain locked until the machine 400 is instructed to dispense the first medication 540 from a canister 410. To dispense the first medication 540 from each individual canister 410, an electronic lock system may open the medication release mechanism. If a medication 540 is sitting on top of the trap door or rotating shutter due to vibration during shipping, the drop sensors 690 in the base station 640 and then the hopper sensors 110 may detect the dispensing of that first medication 540 and the operating sequence continues. If no medications 540 fall when the canister medication release mechanism is opened, then an index wheel or drum 610 as shown in FIG. 6 may be rotated by a motor 620 in the base station 640 until a medication 540 is dispensed. This sequence may reduce the amount of waste and/or the frequency of misdispensed medications 540 into patient packets 580. It also may reduce the time that it takes for the machine 400 to get ready for a batch run, as the machine 400 would not have to open the shutters or trap doors on all of the canisters 410 in the machine 400 before starting a batch run or a PRN (Pro re nata, unscheduled prescription dosage), which might take 10 or 20 seconds and delay the batch run or PRN dosage.

In certain embodiments as shown in FIGS. 4 and 5, an ADU machine 400 may include a cabinet 500 that may be separated into one or more sections. For example, an ADU cabinet 500 may have a top section 440 containing one or more canisters 410, a mid section 450 containing a hopper assembly, and a bottom section 460 containing a packaging mechanism 230. The cabinet 500 may also include a secure locked compartment 240 inside of the ADU cabinet 500 for a nurse or pharmacy technician to return medications 540 that were not administered to patients or residents. In certain embodiments, the cabinet 500 may be designed so that returned medications 540 could be passed through a slit 470 in the front door without the need to unlock the cabinet 500 and open the door 460 to allow the medications 540 to be placed in the secure compartment 240. In certain embodiments, one or more humidity and/or temperature sensors 480 may be placed in the ADU cabinet 500 to detect when the humidity and/or temperature exceed recommended humidity and/or temperature levels for the storage of prescription medications. In certain embodiments, one or more video cameras 280 may be installed in the ADU cabinet 500. For example, as shown in FIG. 5, a video camera 280 may be installed in the packaging station section 230 of the machine 400 to support remote troubleshooting by service technicians.

The packaging mechanism may include packaging film 545 that may be fed by one or more conveyor rollers along with print film 550. The print film 550 may pass by a print head 555, which may be controlled by computer control system 495 to print patient and packet content information onto a particular patient packet 580. Once one or more medications 540 are loaded into patient packet 580, the patient packet 580 may be sealed by heat sealer 560. The sealed patient packets 580 can then be dispensed from the ADU 400 using conveyor system 570.

In certain embodiments, one or more light sensors 110 on top of the hopper 200 may be monitored continuously to detect the release of medications 540 even when the machine 400 is not dispensing. This may provide redundant detection capability with the above sequence that opens the trap door 210 to the secure locked bin 240 before each batch or PRN run, and may further prevent misdispensing if medications 540 fall through the above sensors 110 without being detected.

In certain embodiments, sensors 110 and software may be used to detect when the machine 400 malfunctions, combined with the computer control system 495, to assist with servicing or remote servicing of the machine 400.

In certain embodiments, one or more sensors 110 may be used to sense the status of one or more doors 490 enclosing the interior of one or more sections of the ADU cabinet 500 to permit remote monitoring for unauthorized access to medications 540 within the ADU 400.

In certain embodiments, pharmacy authorization may be required before ADU doors 490 are opened. In certain embodiments, authorized personnel may be able to unlock the doors 490 by using a key or other authorization code or through other authentication methods known to one of ordinary skill in the art.

In certain embodiments, instant messaging capability may be provided between the pharmacy and ADU kiosk users for quicker resolution of issues.

In certain embodiments, the one or more canisters 410 stay locked until the one or more ADU doors 490 are completely locked. Then, the locking canisters 410 may be unlocked as needed to dispense medications 540. When the ADU cabinet 500 needs to be opened for service or to restock medications 540, the locking canisters 410 may be locked before the ADU doors 490 can be unlocked. This may prevent theft of medications 540, as the canisters 410 will always be locked whenever the ADU machine 400 is unlocked.

While the invention has been described with reference to the specific embodiments thereof, it should be understood by those skilled in the art that various changes may be made and equivalents may be substituted without departing from the true spirit and scope of the invention as defined by the appended claims. In addition, many modifications may be made to adapt a particular situation, material, composition of matter, method, operation or operations, to the objective, spirit, and scope of the invention. All such modifications are intended to be within the scope of the claims appended hereto. In particular, while the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations is not a limitation of the invention.

We claim:

1. A method of dispensing medication from a machine, comprising:
    providing a machine comprising one or more base stations configured to receive one or more canisters, a hopper for receiving one or more doses of medication from the one or more canisters, and one or more doors for enclosing and locking one or more canisters in the machine;
    providing one or more canisters comprising one or more medication release mechanisms for selectively releasing one or more doses of medication from the one or more canisters, one or more canister locking mechanisms for preventing the unauthorized removal of doses of medication from the one or more canisters, and containing one or more doses of medication;

connecting the one or more canisters to one or more base stations;

locking the one or more doors;

releasing a selected one or more doses of medication from the one or more canisters into a hopper;

detecting the release of one or more doses of medication into the hopper; and releasing the one or more doses of medication to a packaging mechanism if the detected one or more doses matches the selected one or more doses of medication; and wherein the one or more canister locking mechanisms are configured to prevent unlocking the one or more canister locking mechanisms until the one or more canisters are connected to one or more base stations and one or more doors enclosing the one or more canisters are locked.

2. The method of claim 1, further comprising keeping the one or more canisters locked until the release of a first dose of medication is authorized.

3. The method of claim 1 wherein the one or more doors cannot be unlocked until the one or more canisters are locked.

4. The method of claim 1, wherein the step of detecting comprises continuously monitoring for a period of time to detect the release of one or more doses of medication.

5. The method of claim 1, further comprising locking at least one canister and removing the at least one canister from the machine.

6. The method of claim 1, further comprising releasing the one or more doses of medication to a holding receptacle if the detected one or more doses do not match the selected one or more doses.

7. The method of claim 1, wherein at least one of the medication release mechanisms comprises a retractable portion, the retractable portion having a closed position and a retracted position.

8. The method of claim 7, wherein the step of releasing comprises moving the retractable portion from the closed position to the retracted position to dispense one or more doses of medication from the canister.

9. The method of claim 7, wherein the retractable portion comprises a shutter.

10. The method of claim 7, further comprising locking the retractable portion in at least one of the closed and the retracted position.

11. The method of claim 7, wherein the locking mechanism comprises a worm gear for selectively moving the retractable portion between the closed position and the retracted position.

12. The method of claim 11, wherein the locking mechanism comprises a worm gear for selectively locking the retractable portion in at least one of the closed position and the retracted position.

13. The method of claim 1, wherein the step of sensing is performed continuously for a period of time.

14. The method of claim 1, wherein the step of releasing comprises:

releasing a first dose of medication; and releasing a second dose of medication after the first dose of medication has been detected by one or more sensors.

15. The method of claim 1, wherein the step of releasing comprises:

releasing a first dose of medication; and releasing a second dose of medication after the first dose of medication has been detected by one or more sensors and released to the packaging mechanism.

16. The method of claim 1, further comprising remote monitoring for unauthorized access to the one or more canisters.

17. The method of claim 1, further comprising receiving authorization before opening one or more doors of the machine for accessing the one or more canisters.

* * * * *